United States Patent [19]

Hu et al.

[11] Patent Number: 5,269,931

[45] Date of Patent: * Dec. 14, 1993

[54] CATIONIC CHARGE MODIFIED MICROPOROUS MEMBRANES

[75] Inventors: Ho-Pin Hu; Inessa Katsnelson; Alan Sellinger, all of Ann Arbor; Wesley Tamashiro, Ypsilanti, all of Mich.

[73] Assignee: Gelman Sciences Inc., Ann Arbor, Mich.

[*] Notice: The portion of the term of this patent subsequent to Sep. 29, 2009 has been disclaimed.

[21] Appl. No.: 747,668

[22] Filed: Aug. 20, 1991

Related U.S. Application Data

[63] Continuation-in-part of Ser. No. 583,640, Sep. 17, 1990, Pat. No. 5,151,189.

[51] Int. Cl.$^5$ .............................................. B01D 67/00
[52] U.S. Cl. ................................... 210/635; 210/645; 210/500.39
[58] Field of Search .................... 204/180.1, 180.2; 422/56, 58, 61; 521/53, 54; 210/490, 500.39, 500.42, 500.43, 635, 638; 264/41, 49

[56] References Cited

U.S. PATENT DOCUMENTS

| | | | |
|---|---|---|---|
| 4,512,896 | 4/1985 | Gershoni | 210/635 |
| 4,964,990 | 10/1990 | Kraus et al. | 210/500.39 X |
| 5,006,287 | 4/1991 | Davis | 264/41 |
| 5,151,189 | 9/1992 | Hu et al. | 210/490 X |

Primary Examiner—Frank Spear
Attorney, Agent, or Firm—Krass & Young

[57] ABSTRACT

Cationic charged semihydrophobic polyethersulfone (CSfIP) membranes having hydrophilic and semihydrophobic properties are provided, as well as preparation of the same by post-treatment. Typically, as an illustration, a microporous hydrophilic polyethersulfone membrane substrate which contains non-leachable polymeric additive having functional groups is treated in an alkaline solution for simultaneous or sequential reaction with 1) a primary charge modifying agent which is an epichlorohydrin modified polyamine, and 2) a secondary polymeric charge modifying agent containing a positive charge (or for reaction with the primary charge modifying agent alone); then baked until cured at elevated temperature; and finally washed and dried. The CSHP membranes are used in various applications such as the filtration of fluids and the macromolecular transfer of biomolecules either from electrophoresis gels or directly to immobilization on the membrane for hybridization and stripping. The CSHP membranes—unlike conventional charged membranes which typically show a decrease in sensitivity and reprobing performance—retain their sensitivity and reprobing performance and excel in this regard throughout multiple reprobing cycles.

39 Claims, 8 Drawing Sheets

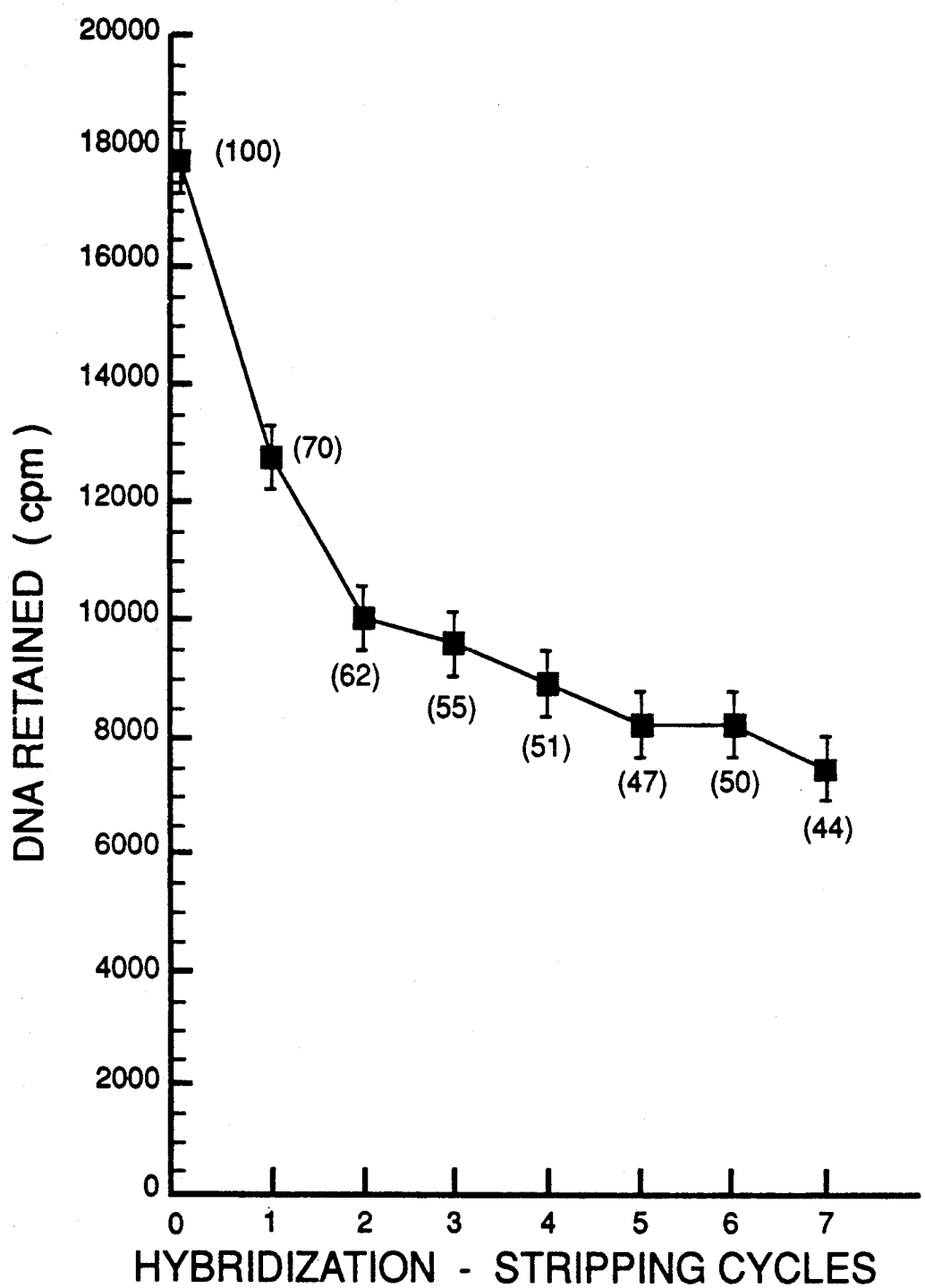
RETENTION OF DNA BY A CATIONICALLY CHARGED, SEMIHYDROPHOBIC, POLYETHERSULFONE MEMBRANE THROUGH MULTIPLE CYCLES OF HYBRIDIZATION AND STRIPPING

CATIONIC CHARGE MODIFIED MICROPOROUS MEMBRANES

CROSS-REFERENCE TO RELATED APPLICATION

This is a continuation-in-part of U.S. patent application Ser. No. 07/583,640 filed Sep. 17, 1990, now U.S. Pat. No. 5,151,189.

FIELD OF THE INVENTION

This invention relates to novel cationic charged semihydrophobic polyethersulfone (CSHP) membranes that have both hydrophilic properties and semihydrophobic properties. The CSFIP membranes are useful for filtration of fluids, for macromolecular transfers, electrophoresis, blotting methods, and the like. In this regard, the CSHP membranes, compared to conventional hydrophilic membranes and hydrophobic membranes, have excellent properties and are substantially better with respect to sensitivity for immobilization of biomolecules, with respect to avoidance of loss of the biomolecule on stripping, and with respect to the number of times cycles of hybridization and stripping can be carried out. More particularly, this invention relates to cationic charge modified microporous membrane media of the type used in medical, genetic and biochemical research and in the food and wine, cosmetics, biotechnology, pharmaceutical, and electronics industries.

BACKGROUND OF THE INVENTION

Microporous membranes are usually defined as thin walled structures having an open spongy morphology with a narrow pore size distribution. The mean pore sizes for microporous membranes typically range between 0.01 µm and 10 µm. Traditionally, microporous membranes are used to remove fine particulate matter such as dust and bacteria from liquids and gases. A microporous membrane can achieve the clarification by different mechanisms. For example, particulates can be retained by microporous membranes through physical sieving of all particulates larger than the pore size of the membranes. In this mechanism, filtration efficiency is governed by the relative size of the particulates and membrane pore size.

Another mechanism in which a microporous membrane can remove suspended particulate materials is the electrokinetic capture mechanism. This is achieved by imparting an appropriate zeta potential to the membrane's internal and external surfaces.

The zeta potential can be either positive or negative depending on the charge of the solid surface. Most suspended particulates which are commonly subjected to removal by filtration have a negative zeta potential. Therefore, such particulates will be readily adsorbed or attracted by solid surfaces that have positive zeta potentials. Based on this, applying a positive zeta potential to the available surface of a microporous membrane will greatly improve the particulate capture capacity of the membrane. This is true even for particulates whose size is much smaller than the membrane pore size. As a result, a high fluid flow rate through the membrane can be maintained using this concept and yet particulate capture by the membrane is much more efficient than indicated by the rated pore size of the membrane.

Attempts to enhance flow rates and to increase membrane life using cationically charged membranes have been made for a number of years. For example, the U.S. Pat. Nos. 4,007,113, 4,473,474, 4,673,504, and 4,708,803 to Ostreicher et al. describe the use of a charge modified filter and process for making the same. U.S. Pat. No. 4,473,475 to Barnes et al. also disclose a cationically charged microporous membrane and its usage. U.S. Pat. No. 4,523,995 to Pall et al. and U.S. Pat. No. 4,604,208 to Chu et al. are other examples of charge modified microporous membranes.

The ability to separate proteins by applying an electric current was described nearly six decades ago. Those early experiments were performed completely in liquid buffer systems and proteins appeared as poorly isolated concentration gradients. Since then, various porous materials (e.g., paper and gels) have been used successfully for the electrophoresis of proteins leading to significant improvements in resolution. Perhaps the most notable of these was the introduction of polyacrylamide gels. When used in conjunction with sodium dodecyl sulfate as a protein denaturant, electrophoresis of proteins through polyacrylamide gels offered high resolution of proteins of varying molecular weights.

Biomolecules (e.g., proteins, nucleic acids, carbohydrate) that have been electrophoresed in gels can be stained by a wide variety of dyes. Based on their position in the gel relative to known standards, certain features about the biomolecules such as molecular weight and isoelectric point of the biomolecule can be ascertained. Hence, electrophoresis is used predominantly to provide physiocochemical information about a biomolecule.

Techniques to transfer and immobilize biomolecules to microporous membranes were developed when it became necessary to identify molecules on the basis of immunological or sequence-based reactivity to given probes. Although methods existed for the immunological detection of biomolecules in gels, the use of microporous membranes offered the following advantages:

1) Shorter assay time—since the biomolecules are exposed to the environment rather than sequestered in a gel, incubation times with the probe and washing times are significantly reduced.
2 Ease of handling—microporous membranes are more durable than gels, especially those made of agar or agarose.
3) Decrease in reagents—the volumes of microporous membranes are much less than those of gels. Hence the volumes of reagents needed to interact with microporous membranes are much less than those needed for gels.

Each of the above mentioned patents is limited to the use of charge modified membranes in filtration applications. However, such charge modified microporous membranes can be used for macromolecular transfer application (e.g., DNA Southern blot) and have already been suggested in U.S. Pat. Nos. 4,512,896 and 4,601,828 to Gershoni and in European patent application 0347755 to Pluskal et al.

The transfer process, also known as "blotting", is defined herein as the steps involved in physically moving biomolecules from a gel matrix to a microporous membrane onto which they become immobilized. The gel matrices include agar, agarose, polyacrylamide or combinations of these. Briefly, the biomolecule-containing gel is placed in direct contact with a microporous membrane. The molecules are forced to move from the gel toward the membrane by electrical current or by fluid flow. Transfer by fluid flow methods can be passive (capillary) or by forced pressure. Forced fluid flow can be by positive or negative (vacuum) pressure.

The term "macromolecular transfer" as used herein refers to processes for transferring biological macromolecules such as nucleic acids and proteins from electrophoresis gels to some type of immobilizing matrix. Of particular importance is nucleic acid bloating, such as DNA blotting. A variety of DNA blotting techniques have been developed in the past. Among them, the most common is referred to as "Southern blotting" in which DNA fragments are separated by chromatographic techniques and then denatured while still in the gel. The gel is neutralized and placed over wicking papers which are in contact with buffer held in a buffer reservoir. The blotting membrane is then placed on top of the gel. As the buffer flows into the gel, DNA is eluted and binds to the blotting membrane, thereby transferring the DNA fragment pattern onto the blotting membrane. The fragment pattern can finally be detected using hybridization techniques employing labeled nucleic acids which are complementary to the specific bound fragments.

DNA blotting membranes presently available are limited to nitrocellulose, charged nylon, charged polyvinylidine difluoride, and activated papers derivatized with diazo containing compounds. The commercial charged blotting membranes are of two types, one being hydrophobic and the other hydrophilic. The first is exemplified by a hydrophobic, charged PVDF membrane produced by a simple coating technique on a hydrophilic or hydrophobic PVDF membrane substrate as described in European Patent Application 0,347,755. The second is exemplified by a hydrophilic, charged membrane produced by treating a hydrophilic membrane, with a charge-containing polymer solution under appropriate conditions as described in U.S. Pat. Nos. 4,512,896 and 4,601,828. Thus, the art coats the charged polymers directly on the major polymer matrix in the membrane substrate and does not concern charging resulting from reaction with additives present in a membrane substrate.

SUMMARY OF THE INVENTION

The present invention, as indicated. concerns cationic charged modified microporous membranes having hydrophilic and semihydrophobic properties and also concerns process means for preparing the same. Each such microporous membrane comprises a microporous membrane substrate comprising a base polymer containing at least one polymeric additive. The membrane substrate is cationically charge modified by post-treatment with a primary charge modifying agent containing high molecular weight polymer exposed at the internal and external microporous surfaces of the membrane. The exposed modifying agent is chemically grafted onto the membrane substrate and therefore the resulting membrane is permanently charged. For example, the data show that a representative CSHP membrane of the invention typically is able to retain 55% of the transfer bound DNA after three hybridization-stripping cycles and 44% of the transfer bound DNA after seven hybridization-stripping cycles (see FIG. 8). The polymeric additive is believed to be the primary charge grafting site, as described hereinafter.

In a preferred embodiment, the thus primary-charge modified microporous membrane is charged further by reaction with a secondary charge modifying agent.

The invention also concerns blotting compositions comprising a sample substrate (e.g., a gel) applied to the CSHP membrane; methods of transferring biomolecules, e.g., directly or from a gel to an immobilizing matrix comprising the primary charge- or primary and secondary-charge modified membrane; methods of retaining immobilized molecules on the matrix through multiple cycles of hybridization and stripping; and the like.

BRIEF DESCRIPTION OF THE DRAWINGS

FIG. 8 is a graph showing retention of DNA by a CSHP membrane through multiple cycles of hybridization and stripping.

DETAILED DESCRIPTION OF THE INVENTION

The cationically charged substrates of this invention comprise microporous membranes—sometimes herein referred to as cationic hydrophilic-semihydrophobic microporous membranes or cationic semihydrophobic polyethersulfone (CSHP) microporous membranes—which have been charge modified with fixed formal charge groups containing a net positive charge.

In this regard, the hydrophilicity and hydrophobicity of a typical membrane of the invention relative to those of conventional hydrophilic and hydrophobic membranes were determined by flat stock wetting and capillary wetting (water wicking assay) procedures. Charged membranes which are currently termed "hydrophobic", such as Immobilon-N ®(Millipore Corp.), are not wettable in either water (surface tension = 72 dynes/cin) or a 23% NaCl solution (81 dynes/cm). Membranes which are classified as "hydrophilic", such as Hybond-N ® (Amersham Corp.) and Genescreen Plus ® (DuPont), are wettable in both liquids. The present cationically charged polyethersulfone membrane is wettable in water, hence the classification as hydrophilic, but not in 23% NaCl, hence the classification as semihydrophobic (Table I below).

The semihydrophobicity of the present membrane is more evident in the water wicking assay. The two hydrophilic membranes used in the testing had wicking rates of 4–5 seconds/13 mm whereas the membranes of the invention in typical cases had wicking rates of 22 minutes/13 mm.

TABLE I

SOAKING AND WICKING WETTABILITIES OF HYDROPHOBIC, HYDROPHILIC AND SEMIHYDROPHOBIC MEMBRANES.

Figure 4:
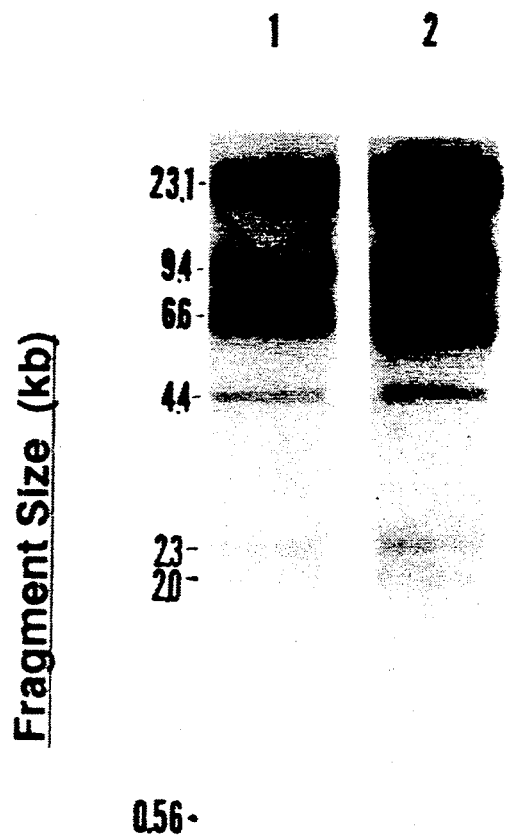
FIG. 4 is an autoradiogram comparing a non-aged CSHP membrane and an aged CSHP membrane in Southern blot performance.

| Membrane | Soaking Wettability (sec) | | Wicking Wettability (min) |
|---|---|---|---|
| | $H_2O$ | 23% NaCl | $H_2O$ |
| Hydrophobic[a] | nw | nw | nw |
| Hydrophilic 1[b] | <1 | 100 | 5 |
| Hydrophilic 2[c] | <1 | 1 | 4 |
| Semihydrophobic[d] | >1 | nw | 22 | nw not wettable
[a]Immobilon-N ® (Millipore Corp.)
[b]Genescreen Plus ® (DuPont/NEN)
[c]Hybond-N ® (Amersham Corp.)
[d]CSHP membrane Charged membranes currently on the market for transfer/immobilization applications show a decrease in sensitivity and reprobing performance with age. As a result, most manufacturers recommend that a membrane be used within 1-2 years from the date of purchase. In contrast, DNA binding experiments with the cationically charged polyethersulfone membrane of the invention typically showed an increase in performance with age (FIG. 4). By comparison with the gel transfer and reprobing performance of freshly made membranes of the invention, the results demonstrated improved performance of the same membranes that were held 8 months at room temperature and 6 months at 50° C.

The term "microporous membrane" as used herein defines a membrane with a pore size range such that the membrane does not retain or reject dissolved proteins or salts from aqueous feed solutions. Preferably, the microporous membrane has an average pore size ranging from 0.05 μm to 10 μm and a water bubble point (WBP) of less than 120 psi.

The preparation of cationically charged microporous membranes described in this invention is based on a post-treatment process. The membrane substrate suitable for the post-treatment must contain at least one non-leachable polymeric additive (preferably at least 2 Wt % with respect to the major matrix polymer in the microporous nienibrane) . The additive enhances hydrophilicity and has functional groups latently reactive with epoxy groups (or the precursor of epoxy groups). A preferred example of a suitable substrate membrane is a membrane comprising polyelhersulfone, described in U.S. Pat. No. 4,900,449, having the formula

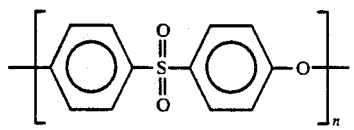

preferably where n is an integer from 50 to 150. This membrane contains the preferred additives polyvinylpyrrolidone and polyethylene glycol as non-leachable, intrinsic wetting agents. The principle chemistry in this invention is based on the chemical grafting of a primary charge modifying agent to the polymeric additive or additives in the membrane substrate. The primary charge modifying agent must contain epoxy groups and/or the precursor of epoxy groups or other functionality which can chemically react with hydroxy and amine groups and other directly reactive groups and latently reactive functional groups; and must contain polyamines which can chemically react with other electrophile containing compounds and impart the positive charge. Polyethyleneimine epichloroliydrin modified resin which is available commercially as SC-86X (Trademark of MorLon-Thiokol, Chicago, Ill.) is the preferred primary charge modifying agent. This resin has the chemical structure I shown below.

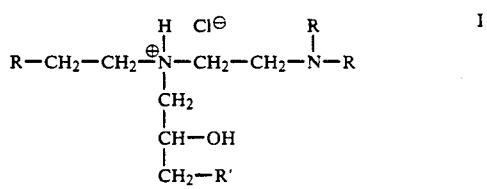

where R independently represents hydrogen or a continuation of the polyamine chain and R' represents —OH or —Cl. The preferred primary charge modifying agent used in this invention is a water soluble polymer of suitable viscosity in water, more preferably having a viscosity in the range from about 10 to 100 centipoise at 17% concentration in water. Other polymers having chemical properties similar to the preferred primary charge modifying agent can also be used.

Since the protonated amino group in the preferred charge modifying agent is not a fixed quaternized amine group and is sensitive to the variance of environmental pH, a secondary charge modifying agent—containing fixed formal positive charge and functional groups which can chemically react with the primary charge modifying agent—can be added according to a preferred embodiment to increase the charge capacity and to decrease the pH dependence of final cationically charged membrane. Preferably, the secondary charge modifying agent is a) partially phosphinated polyvinylbenzyl chloride synthesized by the reaction of polyvinylbenzyl chloride of suitable molecular weight (e.g. 55,000) with trialkyl (or triaryl) phosphine, or b) quaternized poly (dimethylamine-co-epichlorohydrin) of suitable viscosity in water. The latter chemical, which has a viscosity of 40 cps at 39% concentration in water, is commercially available from Scientific Polymer Products, Inc., Ontario, N.Y. The chemical structures II and III of the preferred secondary charge modifying agents are as follows:

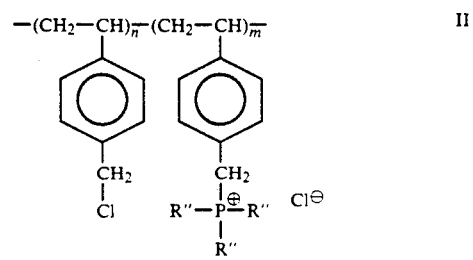

where m and n are integers indicating the polymer length and R" independently represents a lower alkyl group (preferably a $C_{1-4}$ alkyl group) or an aryl group (preferably a phenyl group); and

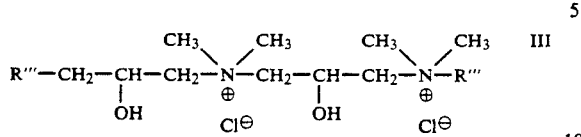

where R''' is a continuation of the polymer chain.

Other secondary charge modifying agents which chemically behave similarly to the aforementioned secondary charge modifying agents can also be used in this invention. For example, ionic species other than phosphonium ions in the partially phosphinated polyvinylbenzyl chloride such as ammonium, sulfonium, or the like which form fixed formal positive charge groups are also suitable in this invention.

The invention in another preferred aspect concerns a process for preparing the described cationic charge modified microporous membrane comprising:

A. providing a microporous membrane substrate, preferably polyethersulfone, comprising at least one non-leachable polymeric additive, preferably selected from polyvinylpyrrolidone and polyethylene glycol, which additive enhances hydrophilicity and has functional groups directly reactive or latently reactive with reactive groups of charge modifying agents;

B. reacting the membrane substrate with a primary charge modifying agent, preferably having structural formula I, by means including baking, said agent being reacted in an amount conferring a positive charge to said membrane substrate; and C. washing and drying the resulting charge modified membrane.

The invention in another preferred embodiment comprises a process for preparing cationic charge modified membranes comprising steps A and B and reacting functional groups of the primary charge modifying agent with a secondary charge modifying agent containing functionality that is reactive with the primary charge modifying agent, the secondary agent being as previously described reacted with the primary agent by means including baking, said secondary agent being reacted in an amount either such that the magnitude of the final formal positive charge is increased over that due to its reaction with the primary agent or such that the sensitivity of the primary agent to the variance of environmental pH is decreased; and washing and drying the resulting charge modified membrane.

The process of preparing the cationically charged membrane in this invention typically includes the following steps:

1. Soaking the microporous membrane in an aqueous solution (or ethanol/water solution in the ratio of 10 Wt % to 30 Wt %) preferably containing 3 Wt % to 7 Wt % of primary charge modifying agent, zero Wt % to 6 Wt % of secondary charge modifying agent, 0.5 Wt % to 3 Wt % of potassium hydroxide (pH=9 to 11), and zero Wt % to 2 Wt % tetrabutylammonium bromide for a sufficient time, e.g., a few seconds, at ambient temperature to wet out the membranes completely;

2. Removing the membranes from the treating solution, wiping off the excess treating solution, e.g., by "squeegee" action using wiper bars, and baking at temperatures and for times sufficient to complete the post-treatment reaction (so that the resulting membrane becomes semihydrophobic as described herein) preferably at 110° C. to 140° C. for 20 to 40 minutes;

3. Washing the membranes preferably in 90° C. deionized water for 20 minutes, and finally drying preferably at 60° C. to 80° C. for 15 to 20 minutes.

The microporous membranes after the above post-treatment typically lose a certain degree of hydrophilicty as compared with the native untreated membranes and behave as semihydrophobic membranes.

The present semihydrophobic membranes exhibit excellent hydrolytic stability. For example, they typically retain their charge capacity and membrane strength after having been subjected to ethanol-Soxhlet extraction for 3 days, 120° C. autoclaving for 40 minutes, or boiling in DI water for 1 hour.

The reaction mechanism of the preferred post-treatment process described above using the preferred membrane substrate and preferred primary and secondary charge modifying agents, may be proposed as follows.

First, under alkaline condition at elevated temperature, the non-leachable polyvinylpyrrolidone present in the membrane substrate undergoes a ring-opening hydrolysis process to form free amine and carboxyl groups which, in situ, react with epoxy groups of the primary charge modifying agent derived from the epichlorohydrin moieties. Simultaneously, the hydroxy groups of non-leachable polyethylene glycol present in the membrane substrate also chemically react with the epoxy groups of the modifying agent to generate the ether linkage. These two reactions result in the charge modifying agents being grafted on the membrane substrate. Further reactions including the self-crosslinking of the primary charge modifying agent under alkaline conditions and the reaction of the primary charge modifying agent with the secondary charge modifying agent may also occur simultaneously. As a result, a cationically charged membrane is produced through this complicated grafting/crosslinking process. While the above is a plausible mechanism for the grafting, it has not been rigorously proven so that this invention is not limited to this or any other theory.

By this mechanism, the major polymer (i.e., polyethersulfone) in the membrane substrate does not play any role in the grafting reaction. This has been proved by control experiments in which a hydrophobic polyethersulfone membrane prepared from a polymer mix containing no active polymeric additives (polyethylene glycol and polyvinylpyrrolidone) was used in the post-treatment process. The result clearly indicated that no detectable charge was present on the membrane after post-treatment. This demonstrates that the presence of active additives in the membrane is essential for the preparation of cationically charged membranes using the post-treatment process disclosed in this invention.

The cationically charged microporous membranes produced by the described process using quaternized poly(dimethylamine-co-epichlorohydrin) as the secondary charge modifying agent wet in water. However, the charged membranes prepared from the treating solution containing partially phosphinated polyvinylbenzyl chloride (assuming 90% conversion from polyvinylbenzyl chloride to phosphinated polyvinylbenzyl chloride based on the stochiometric ratio in the conversion reaction) do not wet when immersed in aqueous solution.

Therefore, these latter membranes must be wetted prior to use (such as use in macromolecular blotting applications) in a water miscible organic solvent which may be either neat or in aqueous solution. The water miscible solvent may be any suitable water miscible solvent such as an alcohol (e.g., methanol, ethanol, or isopropanol).

TESTING METHODS

The following are descriptions of tests performed in the Examples.

Water Bubble Point

This common test for microporous membranes is a measurement of the largest pores in a membrane. It consists of expelling water from a water wetted membrane by air pressure. Pore size and the pressure necessary to remove water from that pore are related by:

$$D = \frac{B \gamma \cos\Theta}{P}$$

where P is the pressure, $\Theta$ is the liquid-solid contact angle between the membrane material and water, $\gamma$ is the liquid-air surface tension, D is pore diameter, and B is a constant.

Water Flow Rate

Water flow rate is the flow rate of wafer passing through the membrane of given dimension, and commonly expressed in seconds/100 mL of water at a given pressure.

Dye Adsorption

Membrane surfaces which have a positive zeta potential will adsorb negatively charged organic dyes. This can be used to semi-quantify the charging efficiency of charged membrane.

Ion Exchange Capacity

The ion exchange capacity is determined as meq per gram of charged membrane by the titration method.

Extractables

The amount of extractables is determined by boiling the membrane in water for one hour and measuring the weight loss.

Latex Sphere Retention

Latex sphere retention measures the particulate removal efficiency of microporous membranes. Briefly, a monodisperse suspension of polystyrene latex with well-characterized particle size is filtered by a membrane under vacuum. The aliquots of filtrate are then analyzed by UV-Vis spectrophotometer at specific wavelength.

Soaking Wettability

The soaking wettability of a microporous membrane was determined by placing a 47 mm membrane disc evenly on the surface of a liquid at ambient temperature. The data are expressed as the time (seconds) taken for the entire disc to become co-extensively and completely wet, e.g., <1 sec or >1 sec.

Water Wicking Wettability

The wicking wettability of a microporous membrane was determined by vertically placing a strip of membrane into a liquid at ambient temperature and measuring the rate at which the fluid moves up the membrane by capillary action. Data are expressed as the time (minutes) required for the water to travel vertically upward for a distance of 13 mm.

The following examples illustrate the invention in greater detail. Since the following examples are for the purpose of illustrating the invention, they are not to be construed as limiting the invention in any way.

ILLUSTRATIVE EXAMPLES

Example 1-Preparation of 0.2 um Polvethersulfone Membrane

Polyethersulfone (Victrex ® TM 5200 available from ICI), dimethylformamide, and polyethyleneglycol 400 were mixed in the ratio of 13:18:69. The mix was stirred to homogeneity and cast at 10-12 mil on glass or stainless steel. Then, the polymer solution was subjected to 60-70% relative humidity ambient air until it became opaque. The membrane was immersed in water to complete coagulation and leach out excess solvent for 2-12 hours, and finally dried at 70° C.

The membrane obtained was instantly water wettable and exhibited 100% bacteria retention when challenged with $10^7/CM^2$ of Pseudomonas diminuta. The membrane had the following characteristics:

| Water Bubble Point | 56 psi |
| --- | --- |
| Water Flow Rate | 22 seconds/9.6 cm$^2$ - 100 mL at 10 psi |

Elemental analysis of the membrane obtained by combustion method indicated the absence of dimethylformamide in the membrane. Nuclear Magnetic Resonance of the dissolved membrane showed that it contained 5 Wt % of polyethylene glycol 400. After Soxhlet extraction using ethanol for two days, this membrane lost its hydrophilicity. Nuclear Magnetic Research of such dissolved membrane showed that it still contained 2 Wt % of polyethylene glycol 400.

Example 2—Preparation of 0.2 um Hydrophobic Polyethersulfone Membrane

Polyethersulfone, dimethylformamide, and sodium bicarbonate were mixed in the ratio of 13.3:53.4:33.3. The membrane was then made by a procedure similar to that described in Example 1. The membrane so obtained however was completely hydrophobic. The membrane characteristics were:

| Water Bubble Point* | 16 psi |
| --- | --- |
| Water Flow Rate* | 120 seconds/9.62 cm$^2$ - 100 mL at 10 psi |

*The membrane sample was prewetted in ethanol prior to water bubble point and water flow rate tests.

Example 3—Preparation of 0.2 um Intrinsically Hydrophilic Polyethersulfone Membrane A casting solution was prepared by mixing polyethersulfone, polyvinylpyrrolidone (available from GAF Corporation, Cincinnati, Ohio) polyethyleneglycol, dimethylformamide, in the ratio of 13:0.2:66.8:20. The membrane was cast and set as in Example 1. The membrane so obtained was spontaneously water wettable. After Soxhlet extraction using ethanol for 3 days, 100° C. water boiling for 30 minutes, or 121° C. autoclaving for 45 minutes, the membrane did not lose its instant water wettability and performance. The membrane performance was:

| | |
|---|---|
| Water Bubble Point | 58 psi |
| Water Flow Rate | 21 seconds/9.62 cm² - 100 mL at 10 psi |

When challenged with $10^7/cm^2$ of *Pseudomonas diminuta*, the membrane exhibited 100% bacteria retention. Elemental analysis of such membrane showed that it contained 1% polyvinylpyrrolidone.

Example 4—Preparation of 0.2 um Intrinsically hydrophilic Membrane

A polymer c&sting solution was prepared by mixing polyethersulfone, polyvinylpyrrolidone, polyetliyleneglycol, and dimethylformamide in the ratio of 13:2:65:20. The membrane was cast and set as in Example 1. The membrane so prepared was instantly water wettable and did not change its hydrophilicity and membrane performance after ethanol Soxhlet extraction for 3 days. Elemental analysis of the membrane prepared indicated that it contained 2% polyvinylpyrrolidone which was about 1% higher than the membrane made in Example 3.

Example 5—Preparation of 0.45 um Intrinsically Hydrophilic Polyethersulfone Membrane A hydrophilic polyethersulfone membrane was made in a process essentially the same as that described in Example 3 except that polyethetsulfone, polyvinylpyrrolidone, polyethyleneglycol, and dimethylformamide in the ratio of 13:0.2:58.8:28 were used to prepare the casting solution. The membrane so prepared had the following characteristics:

| | |
|---|---|
| Water Bubble Point | 33 psi |
| Water Flow Rate | 11 seconds/9.62 cm² - 100 mL at 10 psi |

The membrane obtained had 100% bacteria retention when challenged with $10^7/cm^2$ of *Serratia marcescens*.

Example 6—Preparation of Partially Phosphinated Polyvinylbenzyl Chloride Resin To a 1000-mL round-bottomed flask equipped with a mechanical stirrer and a condenser was added 76 g of polyvinylbenzyl chloride resin (0.5 eq), 118 g of triphenyl phosphine (0.45 eq), and 600 mL of dimethylformamide. This solution was allowed to stir at 75° C. for 16 hours. After cooling, the solution was poured into copious amounts of acetone with vigorous agitation to precipitate the resultant polymer. The powder polymer was isolated by simple filtration and washed with acetone, and finally dried in vacuo at 40° C. for 2 days.

The resultant resin was not soluble in water. However, it was readily soluble in neat methanol or 10% methanol-water mixture.

Example 7—Preparation of 0.2 um Cationically Charged Membrane

The membrane made in Example 3 was placed in an aqueous solution containing 4% polyethyleneimine-epichlorohydrin (SC-86X available from Morton-Thiokol), 2% potassium hydroxide, and 1% tetrabutylammonium bromide for a few seconds, and then was removed from the treating solution. Excess polymer solution was wiped off from the membrane using squeegee bars. The membrane was then baked in a vented oven at 140° C. for 20 minutes. After baking, the membrane was washed with DI water at 90° C. for 20 minutes, and finally dried at 70° C. for 20 minutes. The membrane so prepared was a charged semihydrophobic polyethersulfone (CSHP) membrane and had cationic charge evidenced by anionic dye adsorption. The dye adsorption capacity and the membrane properties such as water bubble point and water flow rate did hot change after ethanol-Soxhlet extraction and autoclaving.

Example 8—Preparation of 0.2 um Cationically Charged Membrane

The polyethersulfone membrane made in Example 3 was soaked in an aqueous solution containing 2% polyethyleneimine-epichlorohydrin (SC-86X available from Morton-Thiokol), 2% poly(dimethylamine-co-epichlorohydrin) (available from Scientific Polymer Products, Inc.), 2% potassium hydroxide, and 1% tetrabutylammonium bromide for a few seconds to completely wet the membrane, and then was removed from the treating solution. Excess resin solution was removed by "squeegee" action using wiper bars. The membrane was then baked in a vented oven at 140° C. for 15 minutes. After curing, the membrane was washed with DI-water at 90° C. for 20 minutes, and finally dried at 70° C. for 15 minutes or longer. The charged semihydrophobic polyethersulfone (CSHP) membrane so prepared showed a strong evidence of the presence of a cationic charge. The characteristics of cationically charged membrane so prepared (water bubble point, water flow rate, dye adsorption and others) did not change after ethanol-Soxhlet extraction, autoclaving and boiling processes, thus demonstrating that the membrane was permanently charged.

Example 9—Preparation of 0.45 um Cationically Charged Membrane

The post-treatment process was conducted in the same manner as described in Example 8 except that the 0.45 um polyethersulfone membrane made in Example 5 was used as the membrane substrate to provide the corresponding CSHP membrane.

Example 10—Preparation of 0.2 um Cationically Charged Membrane

The polyethersulfone membrane substrate made in Example 3 was used in this Example. In addition, ethanol-water mixture (20:80 in weight ratio) was used as solvent to prepare the treating solution. The treating solution was composed of 2% polyethyleneimine-epichlorohydrin, 2% partially phosphinated polyvinylbenzyl chloride, 2% potassiumhydroxide, and 1% tetrabutylammonium bromide. The actual post-treatment processes were carried out in a manner identical to those described in Example 8 to provide the corresponding CSHP membrane.

Example 11—Preparation of 0.45 um Cationically Charged Membrane

A post-treatment was conducted under the same conditions as those of Example 10 except that the 0.45 um polyethersulfone membrane made in Example 5 was used as the membrane substrate to provide the corresponding CSHP membrane.

Example 12—Control Experiments to Corroborate the Necessity of Having Active Additives in the Membrane Substrate to Prepare A Cationically Charged Membrane

Control 12-A

An aqueous solution containing 15% polyvinylpyrrolidone and 2% potassium hydroxide was first boiled for 40 minutes to achieve the base hydrolysis of polyvinylpyrrolidone. The boiled polymer solution had a slightly brown color and showed a remarkably higher viscosity than the non-boiled polymer solution, most likely indicating the occurrence of hydrolysis of polyvinylpyrrolidone after such treatment. The boiled polymer was then cast on a glass plate and cured at 140° C. for 30 minutes to form a brown transparent film. The resultant film was however readily soluble in water as the native polyvinylpyrrolidone film was. This result proved that there was no self-crosslinking of hydrolyzed polyvinylpyrrolidone (or native polyvinylpyrrolidone) under the above conditions.

Control 12-B

An aqueous solution containing 10% polyethyleneimine-epichlorohydrin and 3% potassium hydroxide was cast on a glass plate, and then cured at 140° C. for 30 minutes. The film so formed was completely disintegrated into broken fragments after immersion in water at ambient temperature. This confirms that the self-crosslinked polyethyleneimine-epichlorohydrin is not hydrolytically stable.

Control 12-C

An aqueous solution containing 8.8% polyvinylpyrrolidone and 1% potassium hydroxide was first boiled for 1 hour to accomplish the base hydrolysis of polyvinylpyrrolidone. After cooling the solution to ambient temperature, 7% polyethyleneimine-epichlorohydrin (based on the total weight of final solution) was added with gentle agitation. The final polymer solution was then cast on a glass plate and cured at 140° C. for 30 minutes to form a film. Unlike the films obtained in control 12-A and control 12-B, the film so formed still retained its integrity even after soaking in water at ambient temperature for 24 hours. This demonstrated that the reaction between polyethyleneimine-epichlorohydrin and hydrolyzed polyvinylpyrrolidone occurred, and the resultant film was hydrolytically stable.

Control 12-D

The Soxhlet extracted membrane made in Example 1 was post-treated under conditions similar to those described in Example 8. After post-treatment, the membrane exhibited cationic charge characteristics even after ethanol Soxhlet extraction for 24 hours. This indicated that the non-leachable active additives (polyethylene glycol 400) in the membrane substrate indeed reacted with charging agents in the treating solution.

Control 12-E

The hydrophobic membrane made in Example 2 was subjected to the post-treatment process as described in Example 8 except that it was prewetted by ethanol. Consequently, the treated membrane was still hydrophobic and showed no sign of presence of cationic charge.

Control 12-F

The membrane made in Example 4 was post-treated according to the procedures described in Example 8. However, the CSHP membrane so prepared had a slightly higher charge capacity than the CSHP membrane made in Example 8. This further corroborates that the success of preparing cationically charged membranes using the disclosed method herein is indeed dependent upon the active additives in the membrane substrate. In a certain range, the charge capacity of the cationically charged membranes is a function of the quantity of active additives in the membrane substrate.

Example 13—Anionic Dye Adsorption of Membrane

Dye adsorption testing was done with a dilute aqueous solution (11 ppm) of a negatively charged Metanil Yellow. The solution was filtered through the test samples (47 mm in diameter) at 10 psi and the end point of testing was visually determined and expressed in terms of volume of dye solution when the filtrate penetrating through membrane samples became very light yellow. The membrane samples used in the test and the following tests had a thickness of 5.4 mil±0.6 mil. The accuracy of this dye adsorption test was±15 mL of dye solution. The dye adsorption capacities of membrane samples are set out in Table II below.

TABLE II

| Membrane Sample of Example # | 11 ppm Metanil Yellow Dye Adsorption (mL) |
|---|---|
| 1 | 15 |
| 2* | 20 |
| 3 | 20 |
| 4 | 20 |
| 5 | 15 |
| 8 | 350 |
| 9 | 230 |
| 11* | 300 |
| 12-D | 55 |
| 12-E* | 15 |
| 12-F | 500 |
| Hydrophilic membrane, Genescreen Plus ® | 110 |
| Hydrophobic membrane, Immobilon N ®* | 150 |
| Hydrophilic membrane, Hybond N ® | 25 |

*This membrane was prewetted in ethanol prior to the dye adsorption test.

Example 14—Measurement of Membrane Extractables

The degree of extractables of hydrophilic membranes was determined by pre-weighing the dry membrane samples, then by boiling them in DI-water for 1 hour. After completely drying, the membrane samples were weighed again. The degree of membrane extractables is expressed in terms of percentage of weight loss and shown in Table III below.

TABLE III

| Membrane Sample of Example # | Extractables % |
|---|---|
| 3 | 0.8 |
| 4 | 0.9 |
| 5 | 0.7 |
| 7 | 0.6 |
| 8 | 0.7 |
| 9 | 0.8 |

Example 15—Ion Exchange Capacity of Cationically Charged Membrane

To measure ion exchange capacity, 47-mm discs of membrane samples were soaked in 100 mL of 0.1M HCl for 5 minutes followed by DI water leaching until the water had a pH about 7. After drying of 70° C. for 2 hours, the membrane samples were placed in 100 mL of DI water, to which 2 mL of 5M NaNO3 solution was added, for 10 minutes. Then 51 mL of this solution was removed and titrated with 0.014M AgNO3 using the indicator solution containing 10 drops of 0.1% dichlorofluorescein and three drops of polyethyleneglycol 400 to stabilize the colloidal silver chloride precipitate. The end point of this test was determined by observation of pink color formation from yellow green color. The ion exchange capacity is finally estimated by simple calculation and expressed as milliequivalent/gram of membrane sample shown in Table IV below.

TABLE IV

| Membrane Sample of Example # | Ion Exchange Capacity (meg/g) |
|---|---|
| 3 | 0 |
| 7 | 0.69 |
| 9 | 0.51 |

Example 16—Determination of Degree of Wettability of Various Membranes

To measure the soaking wettability of microporous membranes, 47-mm discs of membrane samples were placed on the liquid surface (water or 23% NaCl solution) at ambient temperature, and the time required for completely wetting out each entire membrane sample was recorded. To measure the water wicking wettability of membranes, the strips of membranes (2"×¾") were vertically placed into water at ambient temperature, and the time required for wicking a 13-mm length of the membrane strips was recorded. The data were shown in Table I.

Example 17—Latex Sphere Retention of Membrane

The particulate removal efficiency of membranes was determined by filtering 30 mL of monodisperse latex spheres (33.3 ppm) suspended in aqueous solution containing 0.1% Triton X-100 at 10 psi. Each 10-mL aliquot of filtrate was collected and analyzed for absorbance by UV-Vis spectrophotometer at 238 nm. The results of these tests are set out in Table V below.

TABLE V

| Membrane Sample of Example # | Sphere Diameter ($\mu$m) | Latex Sphere Retention (%) | | |
|---|---|---|---|---|
| | | 1st 10 mL | 2nd 10 mL | 3rd 10 mL |
| 3 | 0.065 | 15.2 | 3.1 | 3.4 |
| 8 | 0.065 | 100 | 100 | 100 |

Example 18—Southern Blot Analysis of Cationically Charged Membranes

Southern Blot analysis was performed on the CSHP membrane made in Example 9 and on a comparable cationically charged nylon membrane (Genescreen Plus ® nylon membrane available from DuPont NEN). It was found that the transfer of DNA to the membrane made in Example 9 was most efficient under alkaline conditions, whereas neutral transfer of DNA was most efficient for the comparable membrane. Therefore, the membranes were compared under ideal conditions for each membrane.

For Southern blots using alkaline transfers, 1,0, 0.1, and 0.01 ug of lambda DNA, Hind III digest (Life Technologies, Gaithersburg, Md.) was electrophoresed on a 0.8% agarose gel using a TAE buffer system as described by Sambrook et al. (Molecular Cloning, Cold Spring Harbor Press, 1989). Following depurination with 250 mM HCl, DNA was transferred to the membrane samples by capillary action using 0.4N NaOH as the transfer buffer. The DNA was then fixed to the membrane samples by baking at 80° C. for 30 minutes.

For neutral transfers, 1.0, 0.1, and 0.01 ug of lambda DNA, Hind III digest, was electrophoresed on a 0.8% agarose gel as described above. The DNA was depurinated and subsequently exposed to 0.4N NaOH/0.6M NaCl for 30 minutes and to 1.5M NaCl/0.5M Tris, pH 7.5 for 30 minutes. Transfer of DNA to the membrane samples was performed by capillary action using 1.5M NaCl/0.15M sodium citrate as the transfer buffer.

Figure 1:
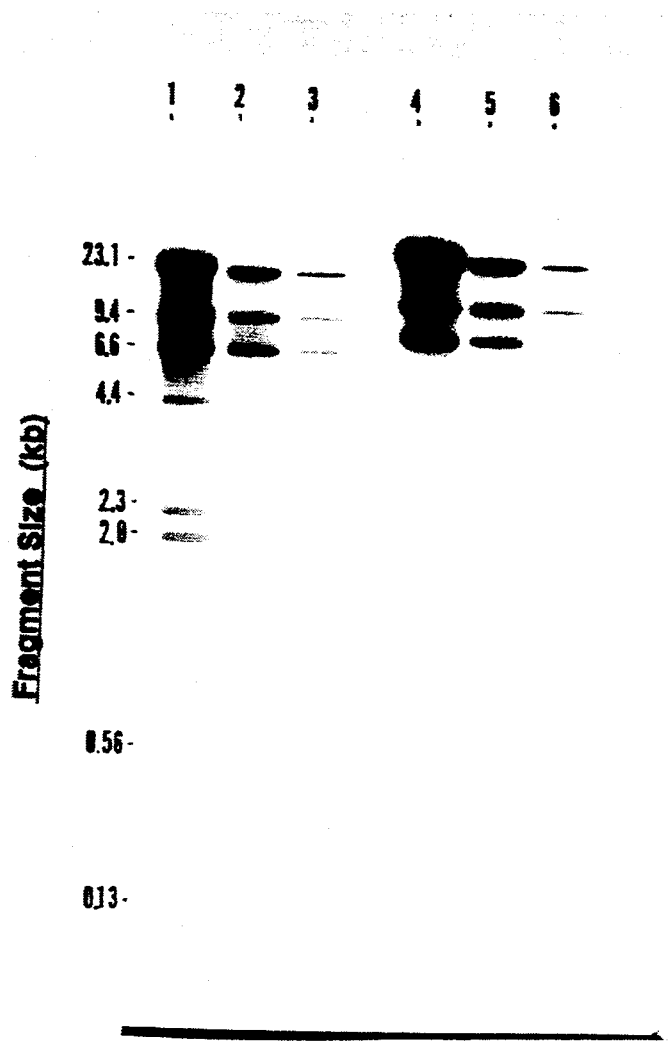
FIG. 1 is an autoradiogram comparing a charged nylon membrane (Genescreen Plus ®, DuPont) to a charged polyethersulfone membrane (a CSHP membrane made as described in Example 9 which follows) using optimal conditions for each membrane in DNA blotting.

A probe was prepared by labelling lambda DNA with deoxycytidine 5'-[$\alpha$-$^{32}$P] triphosphate (Amersham Corp., Arlington Hts., Ill.) using a random primer extension kit (Life Technologies) Hybridization was allowed to proceed overnight at 65° C. The buffers used for hybridization and washing were previously described (Church and Gilbert, PNAS, 81, 1991, 1984). Southern blots were finally exposed overnight to Kodak X-Omat AR film using Lightening Plus ® intensifying screens. The results of charged membrane performance are shown in FIG. 1. These results which are typical show that the CSFIP membrane was more sensitive than the charged nylon membrane.

Example 19—Southern Blot Analysis of Cationically Charged Membranes

Figure 2:
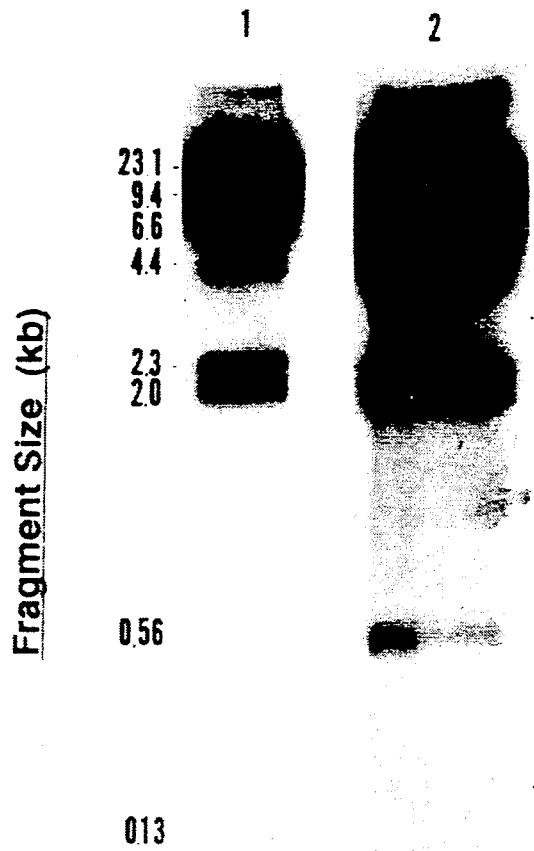
FIG. 2 is an autoradiogram comparing a charged nylon membrane (Genescreen Plus ®) to a CSHP membrane using transfer conditions in Southern blotting.

The CSHP membrane made in Example 9 and a charged nylon membrane (Genescreen Plus ®) were compared using neutral transfer conditions which were optimal for the charged nylon membrane but not optimal for the charged polyethersulfone membrane. Experimentally, 1.0 ug of lambda DNA, Hind III digest, was electrophoresed on a 1.0% agarose gels as described in Example 18. The DNA was then depurinated and transferred to the membrane samples by capillary action using a neutral buffer system. The conditions for neutral transfer, probe preparation, hybridization, and autoradiography were identical to those described in Example 18. The DNA blotting results are presented in FIG. 2. These results confirm that both membranes are satisfactory when using neutral transfer conditions even though alkaline transfer is preferred for the CSHP membrane.

Figure 3:
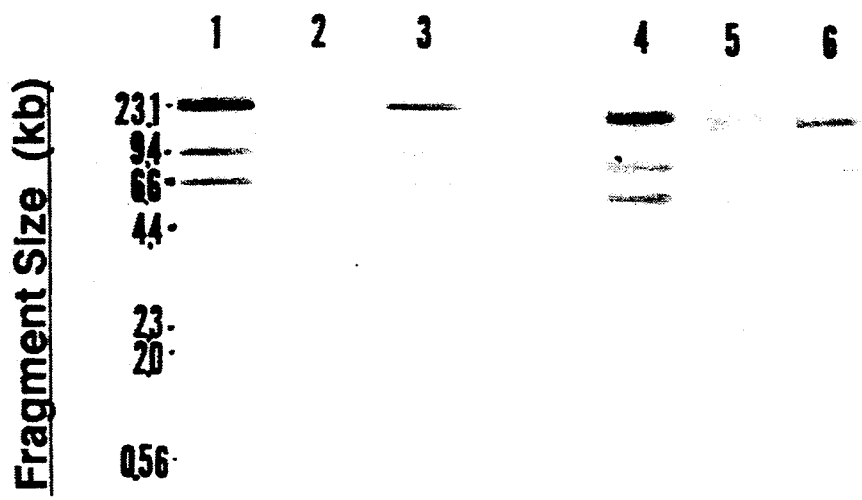
FIG. 3 is an autoradiogram comparing a charged nylon membrane (Genescreen Plus ®) to a CSHP membrane in DNA hybridization/reprobing applications.

Example 20—Suitability of Cationically Charged Membranes in Reprobing Applications Since the ability of a membrane to retain DNA during the probe stripping process is critical, the "reprobability" of the CSHP membrane made in Example 9 and the charged nylon membrane (Genescreen Plus ®) were assessed in this example. The reprobing process was carried out as follows: (1) Lambda DNA, Hind III digest (0.1 ug/lane) was electrophoresed on a 0.8% agarose gel as described in Example 18. The DNA was depurinated as described before and transferred to the membrane samples using a vacuum blotter (Transvac, Hoefer Scientific, San Francisco, Calif.) The methods for probe preparation, hybridization, washing and autoradiography were identical to those described in Example 18; (2) removal or "stripping" of the probe was performed by the alkaline method. A typical stripping procedure involves incubating the membrane samples in 0.4N NaOH at 42° C. for 30 minutes. To simulate 14 stripping cycles, the membrane samples in this test were incubated in 0.4N NaOH at 42° C. for 7 hours. Following the extended stripping cycle, the membrane samples were exposed to Kodak AR film to verify the loss of the probe and subsequently rehybridized with a radio labelled probe to detect DNA which remained bound to the membrane samples. The results obtained from the assay stated above are shown in FIG. 3 and demonstrate that the performance of the CSHP membrane is superior to the charged nylon membrane with respect to loss of the probe on stripping and to multiple stripping cycle efficiency.

Example 21—Effects of Aging on DNA Blotting Performance of the Cationically Charged Polyethersulfone Membrane In this example, the CSHP membrane made in Example 9 and the same membrane which had been baked at 56° C. for 60 days were used in the Southern Blot analysis to compare the blotting performance. Briefly, 0.1 ug of lambda DNA, hind III digest was electrophoresed on a 1% agarose gel using the same TAE buffer system as described in Example 18. The DNA was then depurinated and transferred to the membrane samples under alkaline conditions using a vacuum apparatus. The subsequent processes such as probe preparation, hybridization, washing and autoradiography were similar to those described in Example 18. The results of DNA blotting to cationically charged polyethersulfone membranes are illustrated in FIG. 4 and showed that aging had a beneficial effect on the Southern Blot performance.

Example 22—DNA Gel Transfer to CSHP Membrane

This example describes the transfer of DNA from agarose gels to CSHP membrane followed by hybridization of the membrane-bound DNA with a radiolabelled probe.
1. A submarine gel, with the dimensions of 15×15 cm, was prepared with 1% agarose dissolved in TAE buffer. A 30 well comb was used.
2. Adjacent lanes were loaded with 0.5, 0.25, 0.1, 0.05, 0.01, and 0.001 ug of lambda DNA, Hind III digest, in a final volume of 5 ul.
3. The apparatus was filled with TAE buffer and electrophoresed at 70V for 3h.
4. The DNA was depurinated by soaking the gel in 250 mM HCl for 15 minutes or until the bromophenol blue band turned yellow.
5. CSHP membrane prepared as described in Example 9 was conditioned by prewetting in methanol followed by equilibration in 0.4N NaOH.
6. The gel and membrane were arranged for capillary transfer as described by Sambrook et al. (Molecular Cloning, 1989, Cold Spring Harbor Laboratory Press). Briefly, a piece of absorbent paper (Gelman Sciences, Inc.) was wet in 0.4N NaOH and placed on a glass plate that was elevated in a glass dish. The ends of the absorbent paper overhung the glass plate and acted as wicks. The depurinated gel was placed on the absorbent paper. The equilibrated membrane was placed on the gel. A stack of absorbent papers was placed on the membrane. The dish was filled with 0.4N NaOH transfer buffer. Transfer was allowed to proceed overnight at 25° C.
7. The membrane was removed from the gel and dried at room temperature.
8. DNA was fixed to the membrane by baking at 80° C. for 30-60 minutes.
9. The membrane was placed in a "seal a meal" bag and prehybridized by incubation in BEPS buffer (0.5M phosphate, 1% BSA, 7% SDS, 1 mM EDTA, pH 7.2) for 15 minutes at 65° C. The prehybridization step serves to wash off loosely bound DNA as well as to prevent non-specific binding of the labelled probe in the next step.
10. Decant the BEPS buffer and add fresh BEPS buffer containing a denatured radiolabelled lambda DNA, Hind III digested probe. The probe was denatured by incubation at 100° C. for 10 minutes. 60 ng of lambda DNA, Hind III digest, was labelled with $^{32}P$-dCTP using a random primer extension kit (BRL, cat #8187SA). Free isotope was separated from bound isotope by passing the reaction mixture through a Sephadex G-50 column.
11. Hybridize overnight in a shaking water bath at 65° C.
12. Wash the membranes 3×100 ml (20 min each) at 65° C. in Wash Solution I (40 mM phosphate, 0.5% BSA, 5% SDS, 1 mM EDTA, pli 7.2).
13. Wash the membranes 3×100 ml (20 min each) at 65° C. in Wash Solution II (20 mM phosphate, 1% SDS, 1 mM EDTA, pH 7.2).
14. Wrap the membranes in Saran Wrap and expose to X-Omat AR film (Kodak) using intensifying screens. Note: Do not allow the membrane to dry if reprobing (see Example 23) is to be performed. The length of time for exposure varies depending upon the activity of the probe and the efficiency of labelling.

Figure 5:
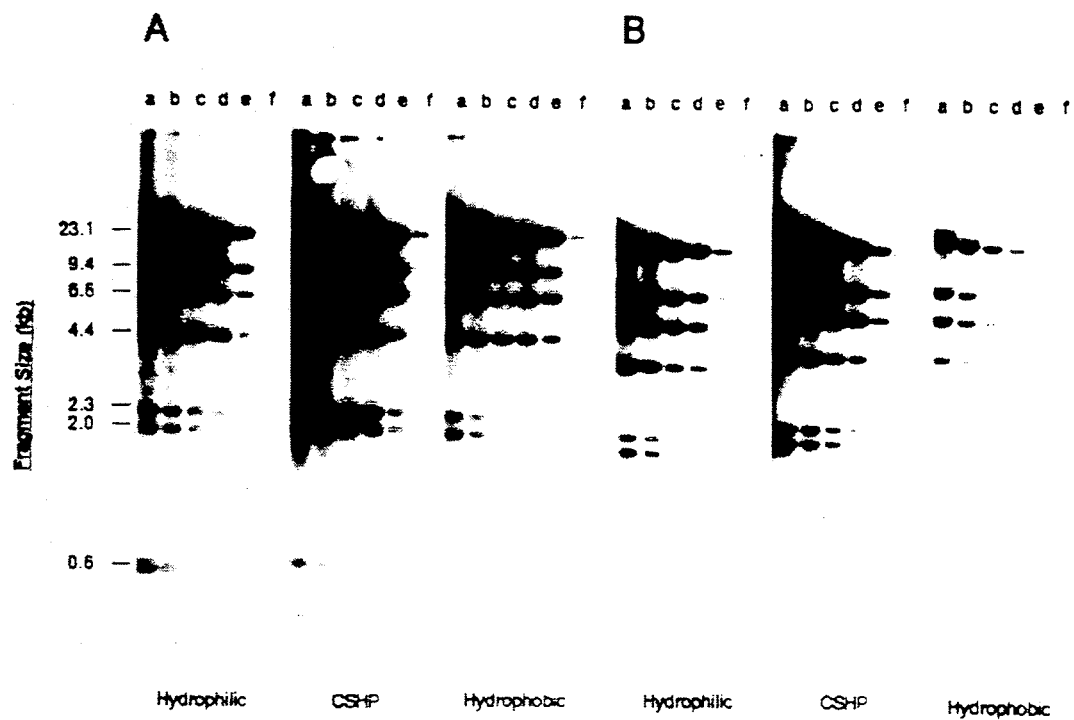
FIG. 5 is an autoradiogram comparing the performance respectively of a charged hydrophilic membrane (Genescreen Plus ®), a charged hydrophobic membrane (Immobilon N ®, Millipore Corp.) and a CSHP membrane, each in capillary (panel A) and vacuum (panel B) transfers of DNA.
Figure 6:
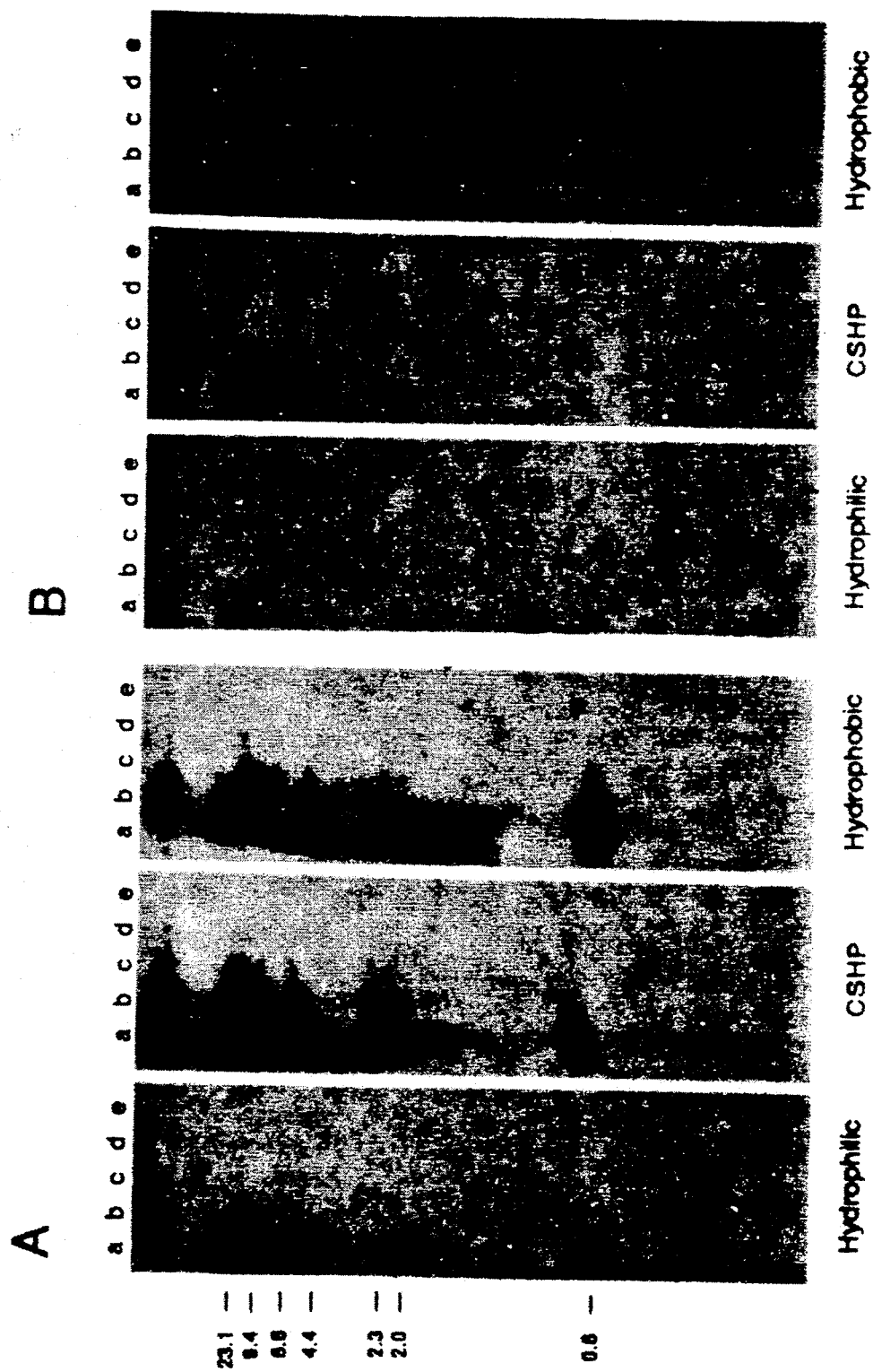
FIG. 6 is an autoradiogram of Southern blots showing the retention respectively of DNA by a charged hydrophilic membrane (Hybond N ®, Amersham Corp. a charged hydrophobic membrane (Immobilon N ®), and a CSHP membrane following 5 cycles of hybridization and stripping.

The results are shown in FIG. 5A. A similar comparison using vacuum transfer is shown in FIG. 5B.

Example 23—Probe Removal

This example describes the removal of probes that have hybridized with DNA bound to the CSHP membrane as made in Example 9.
1. Incubate the wet membrane in 0.4N NaOH for 30-60 minutes at 42° C. on a shaker.
2. Decant the solution and rinse out with 0.4N NaOH to remove residual probe.

Example 24—RNA Gel Transfer to CSHP Membrane

This example describes the transfer and immobilization of RNA to CSHP membrane followed by hybridization with a radiolabelled DNA probe.
1. Pour a 1% horizontal agarose gel containing 10 mM sodium phosphate and 10 mM sodium iodoacetate, pH 7.0 in a 15×15 cm casting tray using a 30-well comb.
2. Mix the following in a sterile, DEPC treated microfuge tube:

| | |
|---|---|
| 40% glyoxal | 1 µl |
| DMSO | 3 µl |
| 50 mM phosphate, pH 7.0 | 1.1 µl |
| RNA (up to 10 µg) | 1 µl |

Incubate at 50° C. for 1 h. Immediately cool on ice until use.
3. Add 1 ul of 6X loading dye to each sample. Centrifuge briefly.
4. Load the sample into the gel and electrophorese in 10 nM phosphate buffer, pH 7.0 at 60–70V until the bromophenol dye has migrated approximately 6–8 cm.
5. Prewet the CSHP membrane in methanol and equilibrate in 7.5 mM NaOH.
6. Assemble the gel, membrane and absorbent paper for a capillary transfer as described in Example 22. Perform a capillary transfer overnight at room temperature using 7.5 mM NaOH as the transfer buffer.
7. Remove the membrane from the gel and air dry. Bake at 80° C. for 30–60 minutes.
8. Prehybridize the membrane in BEPS buffer at 65° C. for 10 min.
9. Decant the buffer and add fresh BEPS buffer containing a denatured radiolabelled DNA probe. Incubate overnight at 65° C.
10. Wash the membranes $3 \times 100$ ml (20 min each) at 65° C. in Wash Solution I (40 mM phosphate, 0.5% BSA, 5% SDS, 1 mM EDTA, pH 7.2).
11. Wash the membranes $3 \times 100$ ml (20 min each) at 65° C. in Wash Solution II (20 mM phosphate, 1% SDS, 1 mM EDTA, pH 7.2).
12. Wrap the membranes in Saran wrap and expose to X-Omat AR film (Kodak) using intensifying screens. Note: Do not allow the membrane to dry if reprobing (see Example 23) is to be performed. The length of time for exposure varies depending upon the activity of the probe and the efficiency of labelling.

Example 25—Protein Transfer to CSHP Membrane

This example describes the transfer and immobilization of proteins to a CSHP membrane as made in Example 9. Visualization of the membrane-bound proteins was accomplished by enzyme immunoassay using a horseradish peroxidase/4-chloro-1-naphthol system.
1. Prepare a 5–20% gradient polyacrylamide gel ($14 \times 16$ cm, Hoefer Scientific) with a 3% stacking gel.
2. Prepare *E. coli* extracts containing 100, 75, 50, 25, and 10 ug of protein per 15 ul in SDS-PAGE sample buffer containing 1.25% mercaptoethanol. Load the preparations on the gel.
3. Remove the gel from the apparatus and equilibrate in $2 \times 200$ ml (15 min per wash) of Tris-Glycine buffer.
5. Wet the CSHP membrane in methanol and equilibrate for 15 min in Tris-Glycine buffer. Wet absorbent pads in the same buffer.
6. Transfer the proteins from the gel to the CSHP membrane using a semidry transfer apparatus (Bio-Trans, Gelman Sciences, Inc.) at 0.8/mamps/cm$^2$ for 2 h.
7. Allow the membrane to dry completely at room temperature.
8. Prewet the membrane in methanol and wet the membrane in 20 mM phosphate buffer containing 0.85% NaCl and 0.05% Tween 20 (PBS-T20).
9. Incubate the membrane in PBS-T20 containing 2% normal goat serum (blocking solution) for 1 h at 37° C.
10. Decant the blocking solution and without washing, add rabbit anti-*E. coli* antiserum at a 1/200 dilution in fresh blocking solution. Incubate for 1 h at 37° C.
11. Wash the membrane $3 \times 200$ in PBS-T20.
12. Add goat anti-rabbit IgG, HRP conjugated, to a dilution of 1/500 in fresh blocking solution. Incubate for 1 h at 37° C.
13. Wash $3 \times 200$ ml in PBS-T20 and $3 \times 200$ in PBS.
14. Incubate the membranes in 4-chloro-1-naphthol substrate solution until the bands are of the optimum intensity (generally 1–2 minutes).
15. Air dry and photograph.

Figure 7:
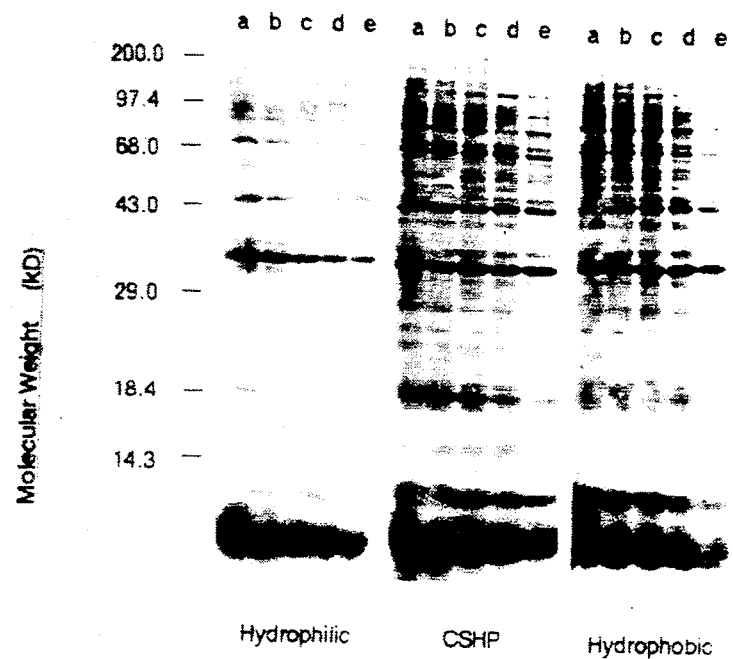
FIG. 7 is an autoradiogram of the performance of a charged hydrophilic membrane (Genescreen Plus ®), a charged hydrophobic membrane (Immobilon N ®) , and a CSHP membrane for the Western blot transfer and immobilization of $E. coli$ proteins followed by immunostaining using a horseradish peroxidase/4-chloro-1-naphthol system.

The results are shown in FIG. 7.

Some of the above examples relate to the transfer of biomolecules (DNA, RNA and proteins) from gels to the CSHP membrane. In each such example, a different buffer is ordinarily used to effect transfer depending upon the biomolecule under investigation. It should be noted that if not stated or exemplified, the specific biomolecule can be diluted in its appropriate transfer buffer and applied directly, rather than transferred from a gel, to CSHP membrane using a pipettor or other applicator device. Hence, the invention involves both the gel transfer and the direct immobilization of biomolecules to the CSHP membrane.

| | |
|---|---|
| Tris | tris(hydroxymethyl)aminoethane |
| EDTA | ethylendiamine tetraacetic acid |
| SDS | sodium dodecyl sulfate |
| BSA | bovine serum albumin |
| dCTP | deoxycytidine triphosphate |
| CAPS | (3-[cyclohexylamino]-1-propanesulfonic acid) |
| DMSO | dimethylsulfoxide |
| Loading dye | (6X stock: 25 mg bromophenol blue, 25 mg Xylene cyanol FF, 1.5 g Ficoll 400 in 10 ml of water |
| HRP | horseradish peroxidase |
| Tween 20 | polyoxyethylene-sorbitan monolaurate |
| Hind III | restriction enzyme from *Haemophilus influenzae* |
| TAE | 40 mM Tris, 1 mM EDTA, 20 mM Acetic Acid, pH 8.0 |
| DEPC | diethyl pyrocarbonate |

Having described the invention, the embodiments of the invention in which an exclusive property or privilege is claimed are defined as follows:

We claim:

1. A cationic semihydrophobic charge modified microporous membrane, comprising:
   a microporous membrane substrate comprising polyethersulfone and at least one non-leachable polymeric additive selected from polyvinylpyrrolidone and polyethylene glycol, which additive enhances hydrophilicity and has functional groups latently reactive with respective groups of charge modifying agents; and
   a primary charge modifying agent comprising polyethyleneimine-epichlorohydrin resin which contains polyamines, can chemically react with electrophile-containing compounds and thus impart a net positive charge, and is chemically grafted to said polymeric additive.

2. A membrane according to claim 1 where the polyethersulfone has the formula

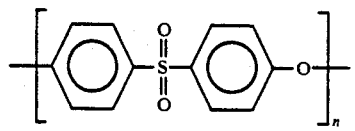

where n is an integer from 50 to 150 and the membrane substrate contains said additive in an amount effective to make the charge modified membrane when formed and dried water wettable.

3. A membrane according to claim 1 where the primary charge modifying agent comprises polyethyleneimine-epichlorohydrin resin having the formula

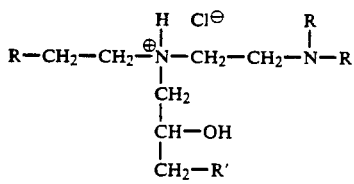

where R independently represents hydrogen or a continuation of the polyamine chain and R' represents —OH or —Cl.

4. A blotting composition, comprising a sample substrate applied to a semihydrophobic charge modified membrane according to claim 1 having an internal surface area and an external surface area, wherein available surfaces of the membrane are coextensively charge modified.

5. The blotting composition as recited in claim 4, wherein the sample substrate comprises a gel.

6. The blotting composition as recited in claim 4, wherein the sample substrate comprises a gel comprising macromolecules selected from the group consisting of DNA, RNA, and proteins.

7. The blotting composition as recited in claim 4, wherein the sample substrate comprises a gel which comprises macromolecules electrophoretically separated into a series of bands.

8. The blotting composition as recited in claim 4, wherein the sample substrate comprises materials capable of being bound by the fixed formal charge of the membrane.

9. The blotting composition as recited in claim 8, wherein said materials comprise amine-containing 10. A method of transferring a biological sample to an immobilizing matrix, comprising applying the sample to a semihydrophobic charge modified membrane according to claim 1.

11. The method recited in claim 10, wherein the biological sample is mixed with a gel and the applying step comprises gel blotting.

12. The method recited in claim 10, wherein the applying step comprises spot-wetting the biological sample to the membrane.

13. The method recited in claim 10, wherein the transferring step comprises electro-transfer of the biological sample to the membrane.

14. The method recited in claim 10, wherein the transferring step comprises capillary-transfer of the biological sample to the membrane.

15. The method recited in claim 10, wherein the membrane comprises polyethersulfone.

16. The method recited in claim 10, wherein the biological sample comprises bacteria.

17. The method recited in claim 10, wherein the biological sample comprises a macromolecule selected from the group consisting of DNA, RNA, and protein.

18. A method of identifying a macromolecule, comprising applying a biological sample which includes the macromolecule to a semihydrophobic charge modified membrane according to claim 1; transferring the macromolecule to the membrane; and detecting the macromolecule.

19. The method recited in claim 18, wherein the applying step comprises spot-wetting the biological sample to the membrane.

20. The method recited in claim 18, wherein the applying step comprises gel blotting.

21. The method recited in claim 18, wherein the macromolecule is transferred by capillary action.

22. The method recited in claim 18, wherein the macromolecule is transferred by applying an electrical current to the biological sample.

23. The method recited in claim 18, wherein the detecting step is accomplished by ELISA.

24. A dot-blot method, comprising applying a biological sample, which includes a macromolecule selected from the group consisting of DNA, RNA, and protein to a semihydrophobic charge modified membrane according to claim 1; and transferring the macromolecule to the membrane.

25. The method recited in claim 24, additionally comprising detecting the macromolecule.

26. A method of colony hybridization, comprising applying a biological sample comprising bacteria to a semihydrophobic charge modified membrane according to claim 1; transferring the bacteria to the membrane; and detecting the bacteria on the membrane.

27. A cationic semihydrophobic charge modified microporous membrane, comprising:
   a microporous membrane substrate comprising polyethersulfone and at least one non-leachable polymeric additive selected from polyvinylpyrrolidone and polyethylene glycol, which additive enhances hydrophilicity and has functional groups latently reactive with respective groups of charge modifying agents; and
   a primary charge modifying agent comprising polyethyleneimine-epichlorohydrin resin which contains polyamines, can chemically react with electrophile-containing compounds and thus impart a net positive charge, and is chemically grafted to said polymeric additive.
   a secondary charge modifying agent containing functionality that is reactive with the primary charge modifying agent, selected from the group consisting of partially phosphinated polyvinylbenzyl chloride, ammonium and sulfonium analogs thereof, and quaternized poly(dimethylamine-co-epichlorohydrin), said secondary agent being reacted with the primary agent in an amount either such that the magnitude of the final formal positive charge is increased over that due to its reaction with the primary agent or such that the sensitivity of the primary agent to the variance of environmental pH is decreased.

28. A membrane according to claim 27 where the polyethersulfone has the formula

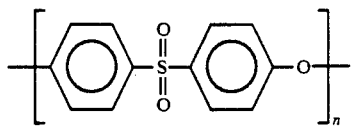

where n is an integer from 50 to 150 and the medium contains said additive in an amount effective to make the charge modified membrane when formed and dried water wettable.

29. A membrane according to claim 27 where the primary charge modifying agent comprises polyethyleneimine-epichlorohydrin resin having the formula

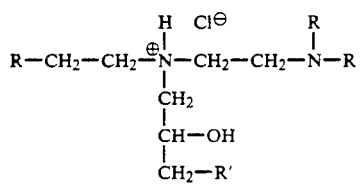

where R independently represents hydrogen or a continuation of the polyamine chain and R' represents —OH and —Cl.

30. A membrane according to claim 27 where the secondary charge modifying agent comprises a partially phosphinated polyvinylbenzyl chloride having the formula

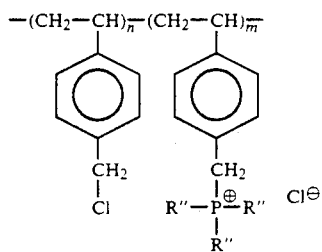

where m and n are integers indicating the polymer length and R" independently represents a lower alkyl group or an aryl group; or an ammonium or sulfonium analog of said phosphinated benzyl chloride.

31. A membrane according to claim 27 where the secondary charge modifying agent comprises a quaternized poly(dimethylamine-co-epichlorohydrin) having the formula

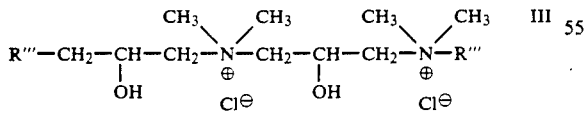

where R''''' is a continuation of the polymer chain.

32. A process for preparing a semihydrophobic cationic charge modified microporous membrane comprising:

A. providing a microporous membrane substrate comprising polyethersulfone and at least one non-leachable polymeric additive selected from polyvinylpyrrolidone and polyethylene glycol, which additive enhances hydrophilicity and has functional groups latently reactive with reactive groups of charge modifying agents;

B. reacting the membrane substrate with a primary charge modifying agent comprising polyethyleneimineepichlorodydrin resin by means including baking, said agent being reacted in an amount conferring a positive fixed formal charge to said membrane substrate when cured; and C. washing and drying the resulting charge modified membrane.

33. A process according to claim 32 wherein the polyethersulfone has the formula

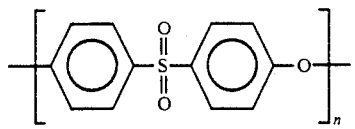

where n is an integer from 50 to 150 and the membrane substrate contains said additive in an amount effective to make the charge modified membrane when formed and dried water wettable.

34. A process according to claim 32 where the charge modifying agent comprises polyethyleneimine-epichlorohydrin resin having the formula

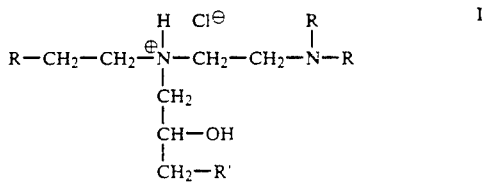

where R independently represents hydrogen or a continuation of the polyamine chain and R' represents —OH or —Cl.

35. A process for preparing a cationic semihydrophobic charge modified membrane comprising:

A. providing a microporous membrane substrate comprising polyethersulfone and at least one non-leachable polymeric additive selected from polyvinylpyrrolidone and polyethylene glycol, which additive confers hydrophilicity and has functional groups latently reactive with reactive groups of charge modifying agents;

B. reacting the membrane substrate with a primary charge modifying agent comprising polyethyleneimine-epichlorohydrin resin in an amount conferring a positive fixed formal charge to said membrane substrate;

C. reacting the primary charge modifying agent with a secondary charge modifying agent containing functionality that is reactive with the primary charge modifying agent, selected from partially phosphinated polyvinylbenzyl chloride, ammonium and sulfonium analogs of said phosphinated benzyl chloride, and quaternized poly(dimethylamine-co-epichlorohydrin), said secondary agent being reacted with the primary agent in an amount either such that the magnitude of the final formal positive charge is increased over that due to its reaction with the primary agent or such that the sensitivity of the primary agent to the variance of environmental pH is decreased; and D. washing and drying the resulting charge modified membrane.

36. A process according to claim 35 where the polyethersulfone has the formula

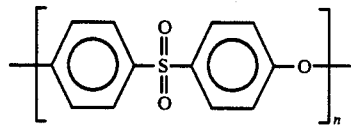

where n is an integer from 50 to 150 and the medium contains said additive in an amount effective to make the charge modified membrane when formed and dried water wettable.

37. A process according to claim 35 where the primary charge modifying agent comprises polyethyleneimine-epichlorohydrin resin having the formula

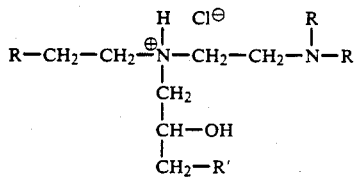

where R represents hydrogen or a continuation of the polyamine chain and R' represents —OH or —Cl.

38. A process according to claim 35 where the secondary charge modifying agent has the formula

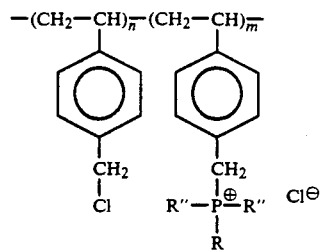

where m and n are integers indicating the polymer length and R" independently represent a lower alkyl group or an aryl group; or an ammonium or sulfonium analog of said phosphinated benzyl chloride.

39. A process according to claim 35 where the secondary charge modifying comprises a quaternized poly(dimethylamine-co-epichlorohydrin) having the formula

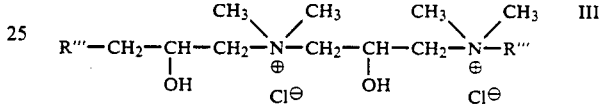

were R'"'" is a continuation of the polymer chain.

* * * * *

UNITED STATES PATENT AND TRADEMARK OFFICE
CERTIFICATE OF CORRECTION

Page 1 of 3

PATENT NO. : 5,269,931

DATED : December 14, 1993

INVENTOR(S) : Hu et al.

It is certified that error appears in the above-identified patent and that said Letters Patent is hereby corrected as shown below:

Title page, item [57], col. 2,
Abstract, line 2, delete "(CSfIP)" and insert --(CSHP)--;

Column 1, line 15, delete "CSFIP" and insert --CSHP--;

Column 1, line 59, delete "unprove" and insert --improve--;

Column 2, line 23, delete "elec(rophoresed" and insert --electrophoresed--;

Column 3, line 7, delete "bloating" and insert --blotting--;

Column 3, line 43, delete "indicated." and insert --indicated,--;

Column 4, line 34, delete "Corp." and insert --Corp.),--;

Column 5, line 52, delete "nienibrane" and insert --membrane--;

Column 6, line 14, delete "MorLon" and insert --Morton--;

Column 7, line 11, delete "R"" and insert --R"'--;

Column 8, line 28, "in situ" should be underlined --in situ--;

Column 9, line 28, delete "wafer" and insert --water--;

UNITED STATES PATENT AND TRADEMARK OFFICE
CERTIFICATE OF CORRECTION

PATENT NO. : 5,269,931
DATED : December 14, 1993
INVENTOR(S) : Hu et al.

It is certified that error appears in the above-identified patent and that said Letters Patent is hereby corrected as shown below:

Column 10, line 29, delete "9.6 $cm^2$" and insert --9.62 $cm^2$--

Column 11, line 13, delete "hydrophilic" and insert --Hydrophilic--;

Column 11, line 14, delete "c&sting" and insert --casting--;

Column 11, lines 15 and 16, delete "polyetliyleneglycol" and insert --polyethyleneglycol--;

Column 11, line 31, delete "polyethetsulfone" and insert --polyethersulfone--;

Column 12, line 8, delete "hot" and insert --not--;

Column 12, line 55, delete "potassiumhydroxide" and insert --potassium hydroxide--;

Column 16, line 24, delete Technologies)"and insert --Technologies).--;

Column 16, line 28, delete "81" and insert --<u>81</u>--;

Column 16, line 33, delete "CSFIP" and insert --CSHP--;

Column 17, line 27, delete "hind" and insert --Hind--;

Column 18, line 29, delete "pli 7.2" and insert --$p^H$ 7.2--;

UNITED STATES PATENT AND TRADEMARK OFFICE
CERTIFICATE OF CORRECTION

PATENT NO. : 5,269,931
DATED : December 14, 1993
INVENTOR(S) : Hu et al.

It is certified that error appears in the above-identified patent and that said Letters Patent is hereby corrected as shown below:

Column 21, line 49, delete "containing" and insert --containing materials.--;

Column 22, line 46, delete "and";

Column 22, line 52, delete "additive" and insert --additive; and--;

Column 23, line 60, delete "R''''''" and insert --R'''--;

Column 24, line 5, delete "polyethyleneimineepichlorodydnn" and insert --polyethyleneimine-epichlorohydrin--;

Column 26, line 30, delete "R''''''" and insert --R'''--.

Signed and Sealed this

Ninth Day of August, 1994

Attest:

BRUCE LEHMAN

Attesting Officer

Commissioner of Patents and Trademarks